United States Patent [19]

Hatfield

[11] Patent Number: 4,574,622

[45] Date of Patent: Mar. 11, 1986

[54] VISCOMETER

[75] Inventor: James C. Hatfield, St. Albans, W. Va.

[73] Assignee: Union Carbide Corporation, Danbury, Conn.

[21] Appl. No.: 593,962

[22] Filed: Mar. 27, 1984

[51] Int. Cl.[4] .......................................... G01N 11/04
[52] U.S. Cl. ...................................................... 73/55
[58] Field of Search ................................ 73/55, 54, 56

[56] References Cited

U.S. PATENT DOCUMENTS

| | | | |
|---|---|---|---|
| 2,503,660 | 4/1950 | Exline et al. | 73/56 |
| 3,302,451 | 2/1967 | Martin | 73/55 |
| 3,327,522 | 6/1967 | Hoyt | 73/55 |
| 3,468,158 | 9/1969 | Sze-Foo Chien | 73/55 |
| 3,713,328 | 1/1973 | Aritomi | 73/55 |
| 3,808,877 | 5/1974 | Blair | 73/55 |
| 4,165,632 | 8/1979 | Weber et al. | 73/55 |
| 4,241,602 | 12/1980 | Han et al. | 73/56 |
| 4,425,790 | 1/1984 | Bice et al. | 73/55 |

FOREIGN PATENT DOCUMENTS 24559 of 1970 Japan ...................................... 73/55

Primary Examiner—Stewart J. Levy
Assistant Examiner—Hezron E. Williams
Attorney, Agent, or Firm—John C. Le Fever

[57] ABSTRACT

A viscometer having the ability of automatically periodically determining the viscosity of liquids having periodic gassing and/or foaming phases comprises pressures taps located on the lower side of a nonvertical portion of a conduit through which the sample liquid is pumped. The viscometer further comprises a three-way valve attached to the pump and means for delaying the pumping of liquid into or out of the pump until the three-way valve has adopted its proper orientation.

18 Claims, 2 Drawing Figures

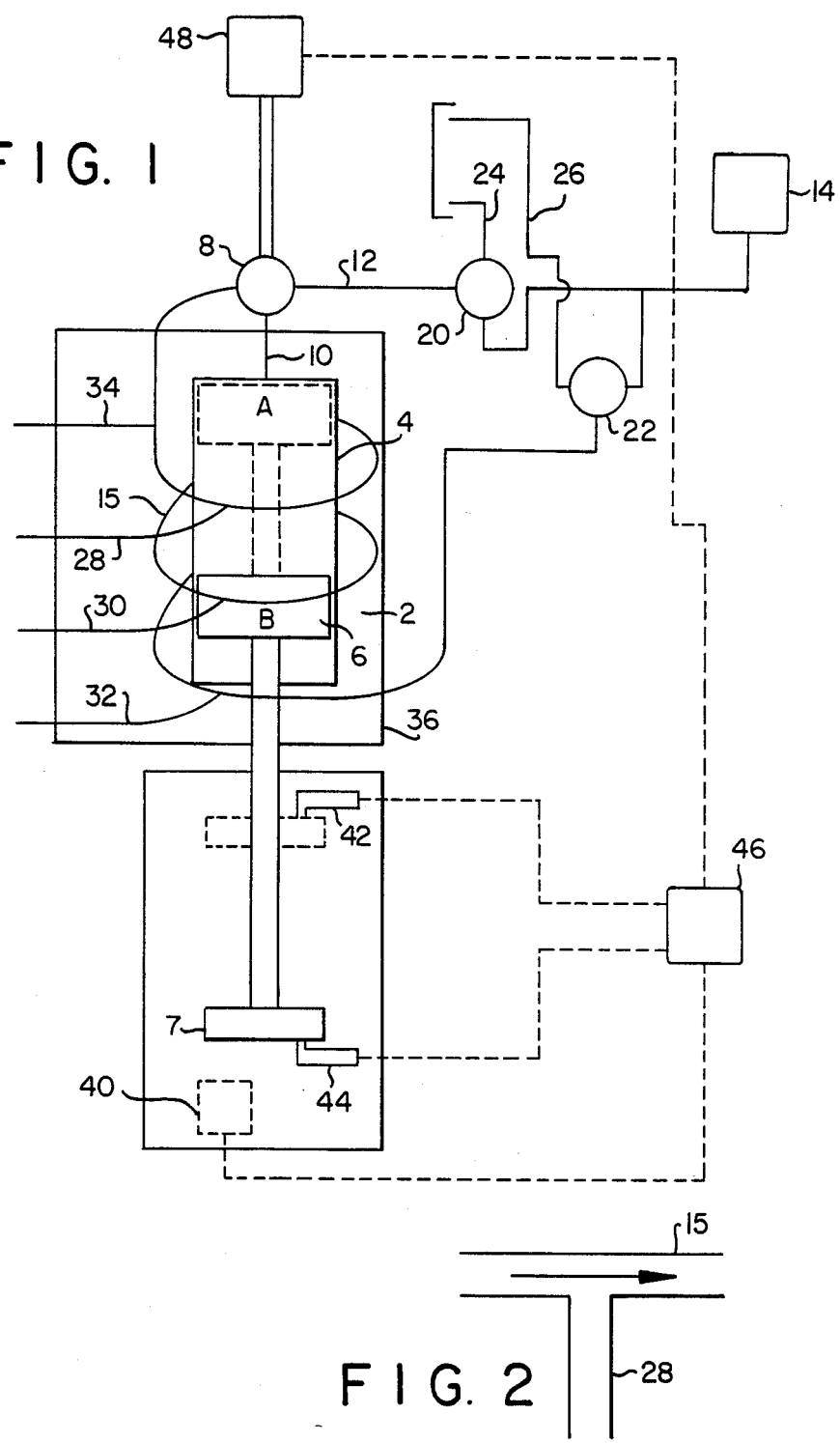

VISCOMETER

FIELD OF THE INVENTION

This invention relates to an apparatus having the capability of continuously and automatically measuring the viscosity of liquid samples of compounds, such as latexes, which periodically foam during their production.

BACKGROUND OF THE INVENTION

Frequently in the production of several chemical compositions it is important to monitor the progress of a chemical reaction in order to determine when the particular reaction has proceeded to a desired point or to determine whether such reaction is proceeding in the desired manner. Often, such monitoring is accomplished by periodically determining the viscosity of the reaction batch mixture. Thus, there is a need for a viscometer which has the capability of automatically periodically determining the viscosity of a selected reaction mixture.

Moreover, many of the chemical reactions whose progress is desirably so monitored periodically generate large quantities of gas. Such gas generation frequently results in the reaction mixture foaming. It is readily apparent that viscometers which operate on the basis of pressure differentials will not be able to determine the rheological properties of foaming liquids as the presence of gas bubbles in the foam will preclude an accurate reading of the pressure exerted by such liquid. However, what is not readily apparent is that when such a foaming fluid has been passed through a viscometer having pressure taps gas bubbles may become trapped at the junction of such pressure taps and the conduit through which the sample liquid is passed due to the configuration of said junction. The presence of these gas bubbles at such sensitive points will interfere with the accuracy of the pressure readings recorded at later stages of the reaction when the liquid has ceased or decreased its gas production and is thus in a form in which its viscosity may be determined. Hence, there is a need for a viscometer which is capable of accurately automatically periodically determining the rheological properties of a liquid which undergoes periodic rapid gas generation phases.

Although several constructions for viscometers have been proposed in the past, these constructions lack the capability of accurately automatically periodically monitoring the viscosity of sample liquids which periodically undergo gassing or foaming periods, such as are encountered in the production of latexes.

For example, U.S. Pat. No. 3,327,522 discloses a device for turbulent friction measurement. This device comprises a manually operated three-way valve which enables samples to be fed into a piston chamber, a piston which compresses the sample liquid through a vertically disposed narrow tube, and pressure transducers whose taps are disposed perpendicularly along the narrow tube. However, because this viscometer is manually operated, such device is not suitable for automatic periodic operation. Moreover, because of the horizontal configuration of the viscometer's pressure taps the device is not suitable for the automatic periodic determination of viscosities of liquids which undergo periodic foaming.

Therefore, it is an object of this invention to provide a viscometer which is capable of automatically periodically monitoring the viscosity of a chemical reaction.

It is another object of this invention to provide a viscometer which is capable of automatically periodically determining the viscosity of a sample liquid which undergoes periodic phases of gassing or foaming.

The foregoing and additional objects will become more fully apparent from the description and examples hereinafter and the accompanying drawings.

SUMMARY OF THE INVENTION

This invention relates to an apparatus for measuring the viscosity of a sample liquid comprising a pump composed of a chamber with a piston disposed therein and being adapted to reciprocate within said chamber between an upper position and a lower position, means for reciprocating said piston between said upper position and said lower position, a three-way valve, a first conduit joined at opposite ends between said valve and said chamber, a second conduit joined at one end to said valve and with another end joinable to a liquid sample reservoir, and a third conduit joined at opposite ends to said valve and said second conduit intermediate the ends thereof, said third conduit having at least one nonvertically disposed portion and at least two spaced pressure taps joined to said nonvertically disposed portion of said third conduit for connection with differential pressure detection means, said three-way valve being arranged to sequentially connect said first conduit and said second conduit when said piston is moving from said upper position to said lower position to feed said sample liquid from said reservoir into said chamber, then to connect said first conduit and said third conduit when said piston is moving from said lower position to said upper position to flow said sample liquid from said chamber into said third conduit; characterized in that said at least two pressure taps are located on the lower side of said at least one nonvertically disposed portion of said third conduit and that the piston reciprocating means further comprises means for delaying reciprocation until said three-way valve has repositioned so as to connect said first conduit with either said second or third conduit.

The viscometer of this invention possesses the ability to automatically periodically determine the rheological properties of liquids which have periodic foaming or gassing phases. This ability stems from the viscometer's construction wherein pressure taps located on the lower section of a nonvertical portion of a conduit are employed and wherein a means for delaying the reciprocation of a pump driven piston are present.

Specifically, as is discussed in some detail below, the construction of the viscometer of this invention is such that gas bubbles which are present in a sample liquid can pass through the sampling conduit of the viscometer without becoming trapped at the pressure tap/conduit junction. Because the presence of gas bubbles at such location will vitiate the obtaining of an accurate measurement of the pressure exerted by the sample liquid, the construction of the viscometer of this invention allows it to sample a liquid reaction which undergoes periodic gassing or foaming phases without requiring the purging the viscometer in order to remove such bubbles between samplings.

Moreover, because the reciprocation means further comprises means for delaying the reciprocation of the piston until the three-way valve has connected the appropriate conduits, the viscometer of this invention is suitable for operating in an automated fashion. Absent such delaying means, the piston would begin to move before the three-way valve has connected the appropriate conduits. Although such appropriate positioning of the valve is not critical when the piston begins its upstroke to force the sample liquid out of the container, such positioning is important when piston begins its downstroke thereby allowing the chamber to be filled. This is because an immediate downstroke will cause a reversal of flow in the third conduit before the three-way valve has rotated so as to close the passage between the third conduit and the second conduit. In consequence small amounts of the previously tested sample liquid will be drawn back into the chamber. When a new sample liquid is drawn from the reactor/reservoir such new sample liquid will mix with the old sample liquid which had been drawn into the chamber by the previous downstroke of the piston. Such mixing of the old and new samples is undesirable since it sacrifices the capability of the viscometer to obtain fresh samples throughout the course of the reaction.

Therefore, because of the location of the pressure taps and the employment of a reciprocation-delaying means, the viscometer of this invention has the ability to accurately periodically automatically determine the rheological properties of sample liquids which periodically undergo gassing or foaming phases. Moreover, by constructing the viscometer out of appropriate materials and by employing a mechanically driven three-way valve which acts as a check valve in the pumping system (vis-a-vis ball-and-seat or flapper valves which become fouled when tacky material is passed through them), the rheological properties of tacky film-forming materials such as latexes may be determined.

BRIEF DESCRIPTION OF THE DRAWING

The present invention will become more apparent from the following description thereof when taken together with the accompanying drawing which is set forth as being exemplary of the present invention and is not intended to be in any way limitative thereof and wherein:

FIG. 1 is a schematic drawing of a preferred embodiment of the viscometer of this invention; and FIG. 2 is an enlarged diagrammatic view of the junction of a pressure tap which is adapted to be connected to a differential pressure detection means and the third conduit of the viscometer of this invention.

DETAILED DESCRIPTION OF THE PREFERRED EMBODIMENT

Turning now to FIG. 1 there is shown a schematic drawing of a preferred embodiment of the viscometer of this invention. This viscometer includes a plunger-type pump 2 which comprises chamber 4 and piston 6, the latter having protruding end 7. Preferably said chamber is composed of stainless steel and said piston of polytetrafluoroethylene. The piston is adapted to reciprocate between upper position A and lower position B within said chamber.

A three-way ball valve 8 is connected to the interior of chamber 4 by first conduit 10. Although first conduit 10 is shown as a discrete section of tubing, it is within the scope of this invention to have first conduit 10 comprise the direct connection of three-way ball valve 8 to chamber 4. Moreover, although a three-way ball valve is shown, it is within the scope of this invention to employ other three-way valves. Second conduit 12 provides a passage between three-way ball valve 8 and sample liquid reactor/reservoir 14. Third conduit 15 provides a passage between three-way ball valve 8 and second conduit section 12. Three-way ball valve 8 is rotationally positioned such that it may sequentially allow passage between second conduit 12 and first conduit 10 and between first conduit 10 and third conduit 15. Optionally and preferably three-way ball valves 20 and 22 are located in second conduit 12 and third conduit 15 respectively. Three-way ball valve 20 is connected to flushing conduit 24 so that it will allow passage between reactor/reservoir 14 and three-way ball valve 8 or alternatively between flushing conduit 24 and three-way ball valve 8. Three-way ball valve 22 is connected to flushing conduit 26 and is positioned such that it will allow passage between reactor/reservoir 14 (via second conduit 12) and three-way ball valve 8 or between flushing conduit 26 and three-way ball valve 8.

At least one portion of third conduit 15 is disposed nonvertically with pressure taps 28, 30 and 32 being located on the lower side of said portion. Preferably, such nonvertical portion is disposed at an angle of not more than about 60° from the horizontal.

The third conduit 15 forms a spiral or helix around the chamber 4. The three-way ball valve 8 which is above the chamber 4, is also above at least two of the pressure taps that are located on the lower side of the nonvertical portion of the third conduit 15.

Pressure taps 28, 30 and 32 are adapted to be connected with differential pressure detection means. Thermocouple 34 is preferably attached to third conduit 15 as shown. Preferably, three-way ball valve 8, pump 2 and the nonvertical portion of third conduit 15 to which pressure taps 28, 30 and 32 are joined are placed within constant controlled temperature bath 36.

The protruding end 7 of piston 6 is coupled to motor 40. First microswitch 42 is activated when piston 6 reaches upper position A. Second microswitch 44 is activated when piston 6 reaches lower position B. Microswitches 42 and 44 are in electrical contact with time delay relay 46, which is in electrical contact with three-way ball valve actuator means 48 and motor 40. Said actuator means may comprise a pneumatic actuator which is controlled by a solenoid in contact with relay 46. Alternatively, an electrical three-way ball valve activator means may be employed. Relay 46 contains circuitry which will delay reciprocation of the piston 6 until three-way ball valve 8 has rotated into its desired orientation. As has been discussed above, the incorporation of such a delaying mechanism is essential for allowing the viscometer to effectively operate on an automatic basis. Thus, without such delaying means, three-way ball valve 8 would still provide an open passage between third conduit 15 and chamber 4 when piston 6 began to reciprocate from upper position A to lower position B. This downstroke would draw previously tested sample liquid from third conduit 15 through three-way ball valve 8 and first conduit 10 into chamber 4. Thus such drawn-back fluid would mix with the new sample liquid drawn into chamber 4 from reactor/reservoir 14. Because time delay relay 46 delays the downstroke of piston 6 from upper position A to lower position B until three-way ball valve 8 has rotated to its appropriate position (i.e. connecting first conduit 10 and second conduit 12 and closing the passage between third conduit 15 and first conduit 10) such problem of sample contamination is effectively eliminated.

Optionally and preferably, motor 40 is connected to means such as a microprocessor having the capability of selectively varying the rate at which piston 6 reciprocates upward during a single upstroke. Such varying of upstroke speed will result in the sample liquid being passed through third conduit 15 (and past pressure taps 28, 30 and 32) at several predetermined flow rates. Obtaining the pressure differentials of the sample liquid at various flow rates will enable a calculation of the apparent viscosity of said sample liquid to be determined. (The calculations involved in such determination are discussed in detail below).

Turning now to FIG. 2, it is seen that pressure tap 28 is connected to the bottom section of a non-vertical portion of third conduit 15. Tap 28 is filled with a fluid, such as distilled water, and joined to from third conduit 15 at a right angle. Tap 28 may be welded or attached by similar means to third conduit 15 or, alternatively, a T-shaped connective coupling may be employed. Sample liquid passing through third conduit 15 in the direction indicated by the arrow presses against the fluid which fills tap 28. This pressure is transferred by said fluid in tap 28 to a differential pressure detection means, such as a pressure transducer. Pressure transducers are well known to those skilled in the art of viscosity determination. One commonly employed pressure transducer comprises a chamber divided by a thin deflectible membrane. Two pressure taps lead into said chamber on opposite sides of said membrane. The pressure differential between said taps is measured by recording the extent and direction of the deflection of the membrane.

The T-shaped intersection which is created by the joining of a pressure tap to a sample conduit can impair the accuracy of a viscometer when a foaming or bubbling sample liquid is passed through the sampling conduit of such viscometer. This is because gas bubbles carried by the sample liquid may become trapped in the pressure tap such that the passage of liquid through the sampling conduit will not carry such bubbles away.

The presence of gas bubbles at such a sensitive area can materially alter the results indicated in the differential pressure detection means to which said pressure tap is connected. The viscometer of the present invention, wherein the pressure taps are located on the lower portion of a non-vertically disposed section of the conduit, substantially overcomes this problem of trapped gas bubbles as such bubbles are not as apt to become trapped in such disposition, and, if trapped, are less likely to remain so.

Now that the components of the preferred embodiment of the viscometer of this invention have been detailed, its mode of operation may be described. The periodically foaming sample liquid (or other liquid as the viscometer of this invention may be used to determine the viscosity of liquids which do not foam or gas) passes from reactor 14 through second conduit 12 past three-way ball valve 8 into chamber 4. During this phase of operation, three-way ball valve 8 is open to first conduit 10 and second conduit 12 but is closed to third conduit 15. When piston 6 reaches lower position B it trips second microswitch 44 which triggers relay 46. Relay 46 serves the double function of (1) immediately triggering three-way ball valve actuator 48 to rotate three-way ball valve 8 so that a passage is open from chamber 4 through first conduit 10 and into third conduit 14 and (2) delaying the reciprocation of piston 6 towards upper position A for a sufficient period of time (e.g. about 3 seconds) until three-way ball valve 8 has rotated into such position. This latter function of relay 46 may optionally be omitted, as allowing the piston to move upwards before the rotation of the three-way ball valve provides an exit for the sample liquid from the chamber will increase the compression exerted by the pump on such sample liquid.

The rotation of three-way ball valve 8 will open a path from chamber 4 into third conduit 15 and will close the path from second conduit 12 via first conduit 10 into chamber 4. Thus, when piston 6 begins its upward stroke toward upper position A the liquid sample within chamber A will be forced through first conduit 10, past three-way ball valve 8 and into third conduit 15.

The pressure exerted by the sample liquid in third conduit 15 is detected by means of pressure taps 28, 30 and 32 and its rheological properties are determined by means well known to those skilled in the art.

The calculations involved in the determination of such rheological properties are discussed in some detail in *Transport Phenomena*, R. B. Bird, W. E. Stewart, E. N. Lightfoot, John Wiley & Sons, N.Y. (1960) and in A. B. Metzner, J. C. Reed, "Flow of Non-Newtonian Fluids—Correlation of the Laminar, Transition, and Turbulent-flow Regions". A.I.Ch.E. Journal, Vol. 1, No. 4, p. 436 (1955). Thus, for Newtonian fluids, such as latexes having less than about 25 weight percent total solids, a single measurement of the pressure drop ($\Delta P$) over a known length of tubing (L) at a known flow rate (Q) and tubing radius (R) is sufficient to determine the viscosity ($\mu$). The Hagen-Poiseuille law gives the relationship among these parameters:

$$Q = \pi \cdot \Delta P \cdot R^4 / 8\mu L$$

For non-Newtonian fluids, such as latexes having total solids contents of from about 25 to about 65 weight percent rheology is well-fitted by the power law fluid model given by $$\tau = K\gamma^n$$

where $\tau$ is the shear stress, $\gamma$ the shear rate, and K and n are adjustable parameters. For a power law fluid, the analogy of the Hagen-Poiseuille law is:

$$Q = \left( \frac{R\Delta P}{2L} \right)^{1/n} \left( \frac{\pi R^3 n}{3n + 1} \right)^{-1/n} K$$

Operating in a mode wherein the piston moves upward at a constant speed, the viscometer generates $\Delta P$ information at a constant Q. Whether the latex is Newtonian or non-Newtonian, this is sufficient to derive the shear stress at the tubing wall which is the maximum shear stress the fluid "sees" in the viscometer. The shear stress at the wall $\tau_w$, is given by $$\tau_w = R\Delta P / 2L$$

Operated in a mode (e.g. by a microprocessor) wherein the piston moves upward at a variable speed, the pressure drop ($\Delta P$) at more than one flow rate (Q) can be determined. At least two different Q's must be run to calculate constants n and k above. When the data are plotted as log Q (ordinate) vs. log P (abscissa), n is the reciprocal of the slope and K is given by $$K = \left( \frac{n\pi D^3}{8(3n+1)} \right)^n \cdot \frac{D}{4LY^n}$$

where D is the tubing diameter and Y is the inverse log of the intercept with the log Q axis. Once n and K are determined, the shear rate at the wall, $\gamma_w$ is found from the Rabinowitsch equation.

$$\gamma_w = \frac{8Q(3n+1)}{n\pi D^3}$$

Thus, the apparent viscosity, $\mu_A$, is $$\mu_A = \tau_w / \gamma_w$$

Because the pressure of the sample is detected by pressure taps located on the lower side of a nonvertical portion of the third conduit, the sample tested is substantially free of gas bubbles which could vitiate the determination of the rheological properties of the sample. The liquid is forced through the third conduit 15 through three-way ball valve 22 into the second conduit and back to the reactor.

When piston 6 has forced all of the sample liquid out of chamber 4, and has thus reached upper position A, protruding end 7 of said piston trips first microswitch 42. This triggers relay 46 into (1) immediately activating three-way ball valve actuator means 48 such that three-way ball valve 8 rotates to open a passage between second conduit 12 and chamber 4 (via first conduit 10); and (2) delaying the downward stroke of piston 6 until three-way ball valve 8 has so rotated. This delay in the downward reciprocation of piston 6 will prevent undesirable sample contamination.

If desired, relay 46 could be adjusted so that the reciprocation of the piston and consequent tripping of first microswitch 42 and second microswitch 44 would cause rotation of three-way ball valves 20 and 22 such that every sampling run could be followed by a flushing run.

EXAMPLE

The following Example is intended to further illustrate the invention and is not intended to limit the scope of the invention in any manner.

A viscometer having a construction similar to that shown in FIG. 1 was connected to a latex reactor. The viscometer comprised a stainless steel cylinder with a polytetrafluoroethylene piston disposed therein. The cylinder was connected to a pneumatically-actuated ¼ inch stainless steel three-way ball valve (Whitey #SS-43X54) with an air-driven actuator (Whitey #MS-153) by a first 0.125 inch diameter stainless steel conduit. Two manually operated ⅛ inch stainless steel three-way ball valves (Whitey #SS-41X52) were placed into second and third conduits, which conduits were 0.125 inch diameter stainless steel pipes. These ball valves were connected to flushing conduits. The viscometer was mounted inside a one gallon stainless steel beaker which was filled with ethylene glycol, the temperature of which was regulated by a solid state relay (Princo Model T-688) to turn a 500 watt knifeblade heater on and off.

The piston was powered by a Harvard syringe pump (Model 975) with a synchronous Bodine motor (Type 34TIBEHY) having 115 inch-ounces of torque which was connected to a Dayton Time Delay Relay #5X828B which was in turn connected to the pneumatic actuator. The pressure taps comprised ⅛ inch stainless steel conduits which were filled with distilled water and connected to the third conduit by means of a Swagelok TM T-shaped tube fitting. These taps were connected to a series of Validyne transducers (DP-15 cells connected to a CD-280 carrier/demodulator).

A latex production reaction was carried out in a reactor to which the viscometer was attached. A 6 ml latex sample was withdrawn every stroke. The pump was set at a setting which pumped 0.04858 ml/sec. The relay was set for a 0 second delay of pump motor before discharge and a 3 second delay before suction. The distance between the pressure taps was 26.2 cm, said taps being conducted to a 0.5 psi transducer. The temperature of the ethylene glycol bath in which the viscometer was placed was maintained at 75° C. The automatic periodic viscosities found during such run are shown in Table 1 below.

TABLE 1

| RUN TIME (HRS) | TOTAL[1] SOLIDS (Wt. %) | "RELATIVE VISCOSITY" |
|---|---|---|
| 0.0 | — | — |
| 0.25 | — | — |
| 0.40 | — | 4.4 |
| 0.50 | 0 | 0.5 |
| 0.52 | 18.6 | — |
| 0.54 | — | 4.0 |
| 0.75 | — | 0.8 |
| 1.00 | — | 1.1 |
| 1.02 | 26.2 | — |
| 1.25 | — | 2.2 |
| 1.50 | — | 4.4 |
| 1.55 | 32.6 | — |
| 1.75 | — | 7.9 |
| 2.00 | — | 16.6 |

[1]As determined by analytical dehydration.

The term "relative viscosity" as employed in the Table above is the shear stress at the third conduit wall expressed as a percent of the maximum wall shear stress encountered during the latex run. The erratic nature of the pumping cycles seen at 0.40 and 0.54 hours into the run is normal. It occurs because the viscometer is filled with degassing water causing random pressure pulses. After about the first half hour, the recorded pressure drop stabilizes, gradually increasing as the total solids increases and the latex thickens.

The example above demonstrates that the viscometer of this invention has the capability of automatically periodically determining the rheological properties of sample liquids which undergo periodic gassing and/or foaming phase. The example also shows that the viscometer of this invention can be constructed so as to have the capability of determining the rheological properties of tacky film-forming liquids.

What is claimed is:

1. An apparatus for measuring the viscosity of a sample liquid comprising a pump composed of a chamber with a piston disposed therein and being adapted to reciprocate within said chamber between an upper position and a lower position, means for reciprocating said piston between said upper position and said lower position, a three-way valve, a first conduit joined at opposite ends between said valve and said chamber, a second conduit with one end joined to said valve and with another end joinable to a reservoir, and a third conduit joined at opposite ends to said valve and said second conduit intermediate the ends thereof, said third conduit having at least one nonvertically disposed portion and at least two spaced pressure taps joined to said nonvertically disposed portion of said third conduit for connection with differential pressure detection means, said three-way valve being arranged to sequentially connect said first conduit and said second conduit when said piston is moving from said upper position to said lower position to feed said sample liquid from said reservoir into said chamber, then to connect said first conduit and said third conduit when said piston is moving from said lower position to said upper position to flow said liquid sample from said chamber into said third conduit; characterized in that said pressure taps are located on the lower side of said nonvertically disposed portion of said third conduit, and that the piston reciprocating means further comprises means for delaying reciprocation until said three-way valve has repositioned so as to connect said first conduit with either said second or third conduit.

2. The apparatus of claim 1 wherein said three-way valve is a three-way ball valve.

3. The apparatus of claim 2 wherein said chamber, three-way ball valve, first conduit, second conduit and third conduit are composed of stainless steel and said piston is composed of polytetrafluoroethylene.

4. The apparatus of claim 1 wherein said means for delaying reciprocation is a time-delay relay.

5. The apparatus of claim 1 including a pneumatic activator for activating said three-way valve.

6. The apparatus of claim 1 including an electric actuator for activating said three-way valve.

7. The apparatus of claim 1 wherein a second three-way valve and a third three-way valve, each adapted to be connected to flushing conduits, are located in the second conduit and third conduit respectively.

8. The apparatus of claim 7 wherein said second three-way valve and said third three-way valve are three-way ball valves.

9. The apparatus of claim 1 wherein said means for delaying reciprocation further includes means for pumping the liquid sample through the third conduit at varied predetermined varied rates.

10. The apparatus of claim 9 wherein the pumping means comprises a microprocessor.

11. The apparatus of claim 1 wherein said chamber, piston, three-way valve, and said nonvertical portion of said third conduit to which said at least two pressure taps are connected are disposed within a constant temperature bath.

12. The apparatus of claim 11 wherein a thermocouple is attached to said third conduit.

13. The apparatus of claim 1 wherein a second liquid is provided in at least one of said pressure taps.

14. The apparatus of claim 13 wherein said second liquid is distilled water.

15. The apparatus of claim 13 wherein said third conduit and said pressure taps are in fluidic contact for transferring sample liquid pressure through said second liquid to said differential pressure detection means.

16. The apparatus of claim 1 including a sample liquid wherein said sample liquid has a periodic foaming phase.

17. The apparatus of claim 1 wherein said third conduit forms a helix around said chamber.

18. The apparatus of claim 1 wherein at least two of said pressure taps are below the horizontal plane formed by said three-way valve.

* * * * *